United States Patent [19]

Arroyo

[11] Patent Number: 4,681,109

[45] Date of Patent: Jul. 21, 1987

[54] SURGICAL INSTRUMENTATION FOR BLOOD VESSELS

[76] Inventor: Juan Arroyo, 12200 SW. 93 St., Miami, Fla. 33186

[21] Appl. No.: 876,109

[22] Filed: Jun. 19, 1986

Related U.S. Application Data

[63] Continuation-in-part of Ser. No. 791,498, Oct. 25, 1985, which is a continuation-in-part of Ser. No. 743,940, Jun. 12, 1985, Pat. No. 4,630,608.

[51] Int. Cl.$^4$ .................... A61B 17/08; A61B 17/00
[52] U.S. Cl. .................................. 128/335; 128/346
[58] Field of Search .............. 128/335, 346, 325, 326, 128/334 C

[56] References Cited

U.S. PATENT DOCUMENTS 4,316,470 2/1982 Braun et al. .................... 128/346

Primary Examiner—Richard C. Pinkham
Assistant Examiner—Gary Jackson
Attorney, Agent, or Firm—John Cyril Malloy

[57] ABSTRACT

Surgical instrumentation in the form of a clamp assembly specifically structured to position and maintain sections of blood vessels, including both veins and arteries, in a preferred surgical orientation such that open ends of the vessel sections are substantially adjacently positioned relative to one another and properly exposed and oriented so that such section ends may be sutured or otherwise secured together. The clamp assembly is structured such that vessel sections to be attached are adjustably positionable so that placement of the section ends may be adjusted and changed to insure proper relative positioning to one another in a preferred exposed position for attachment.

47 Claims, 73 Drawing Figures

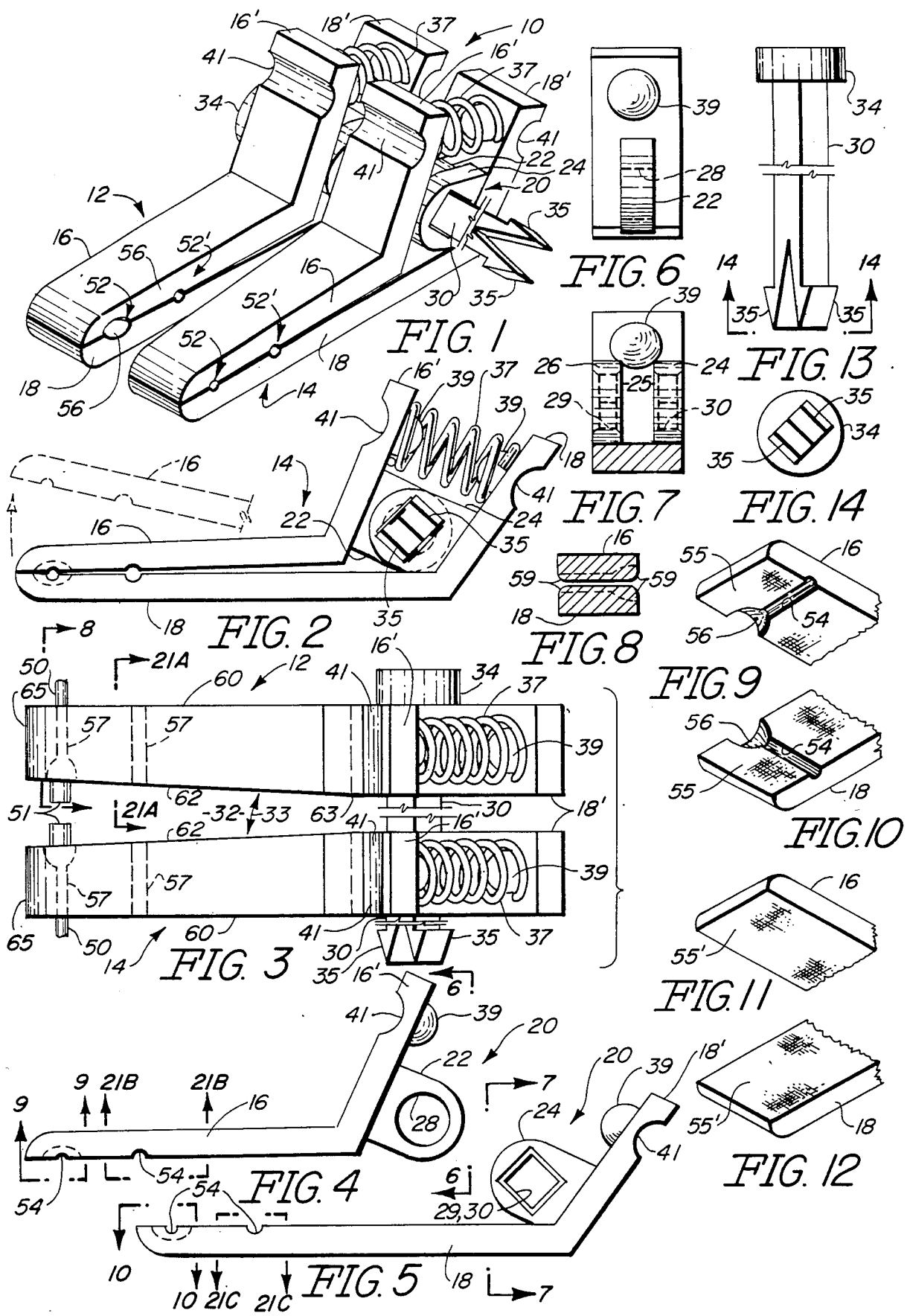

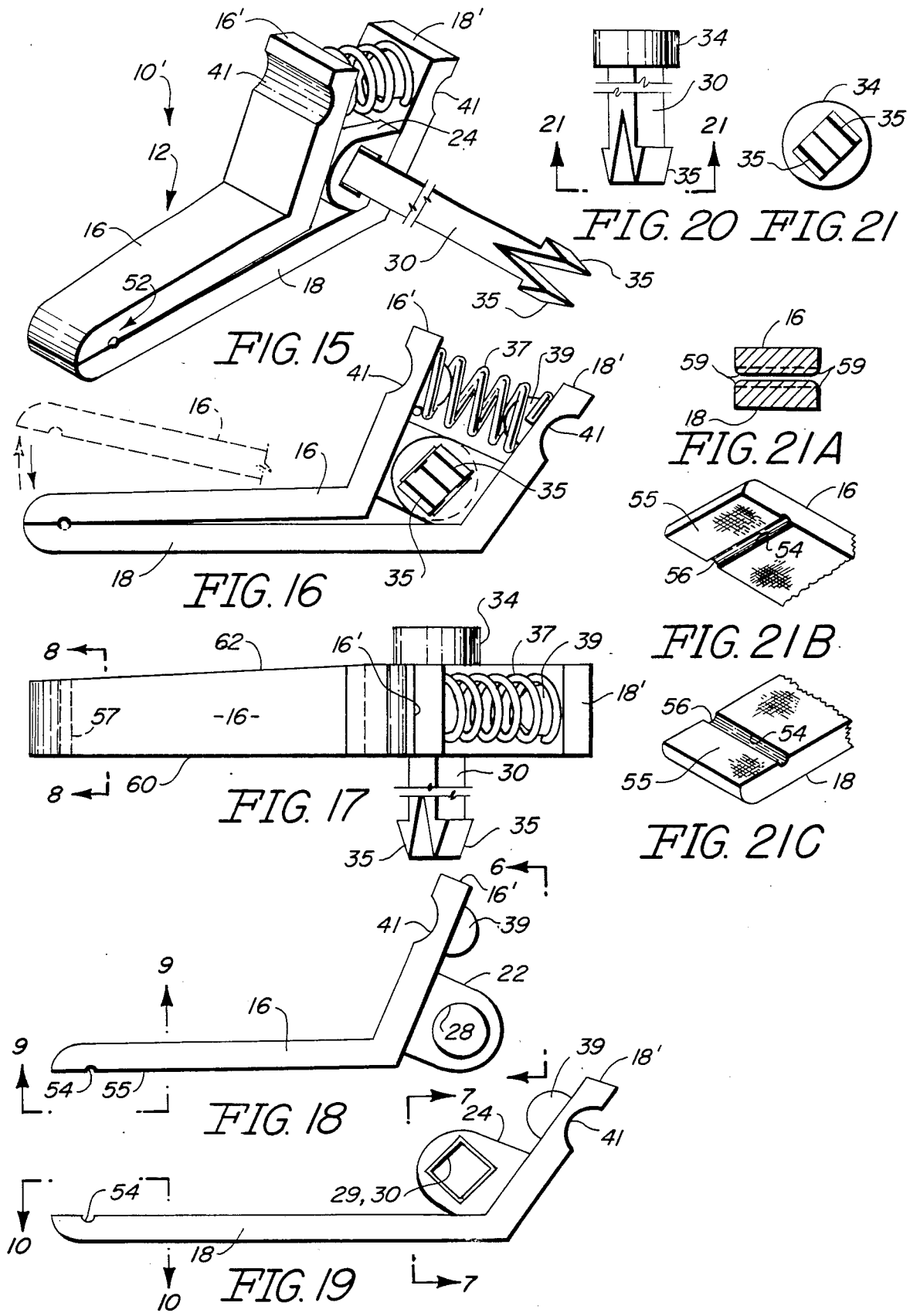

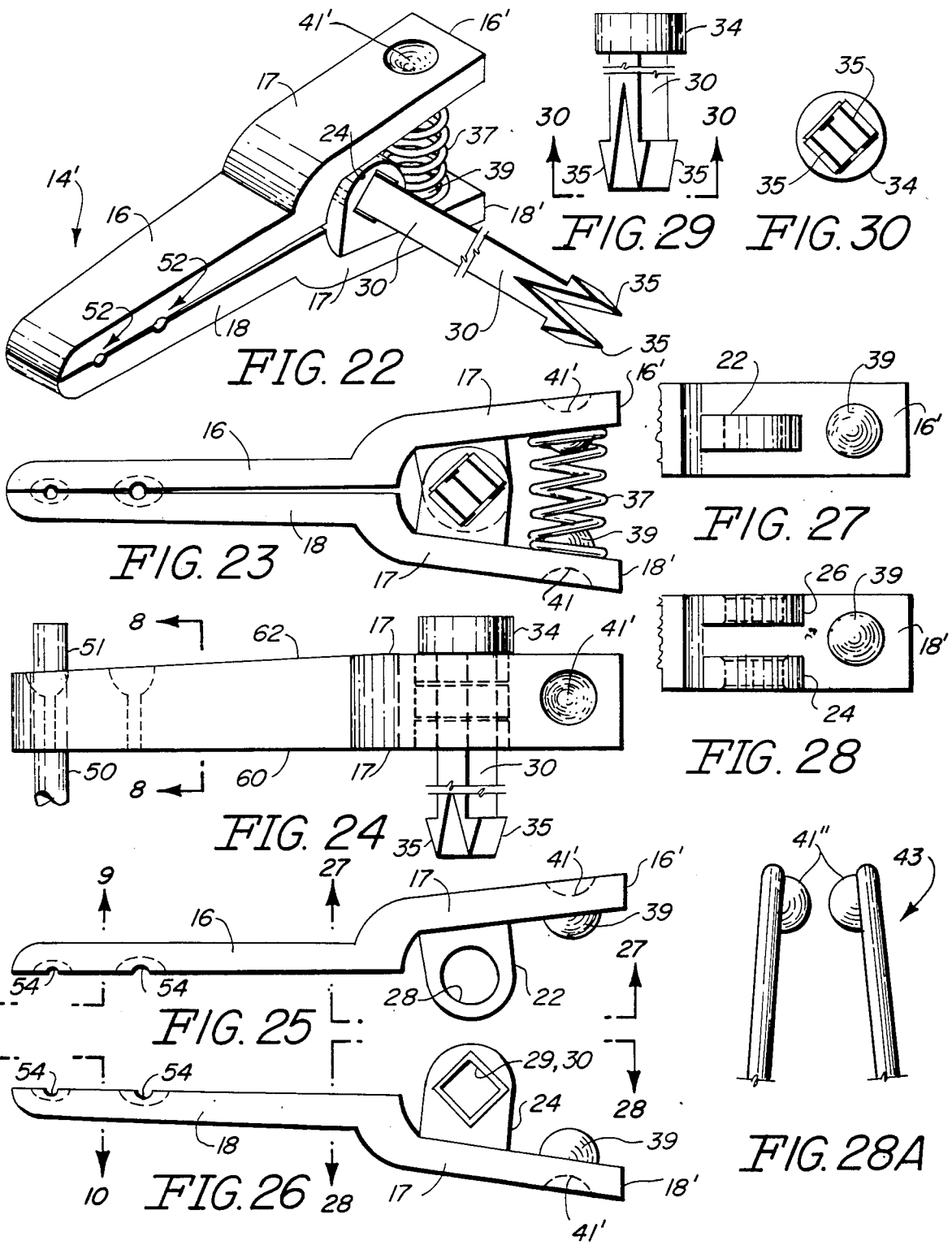

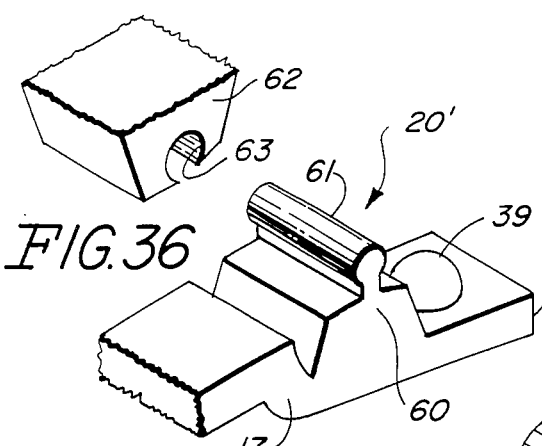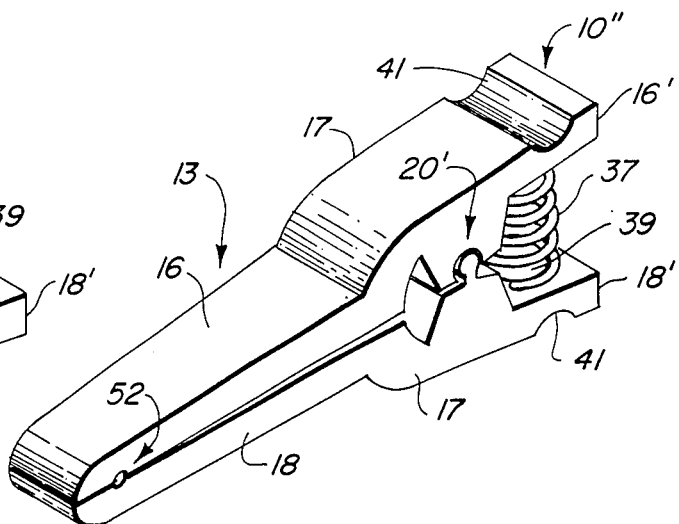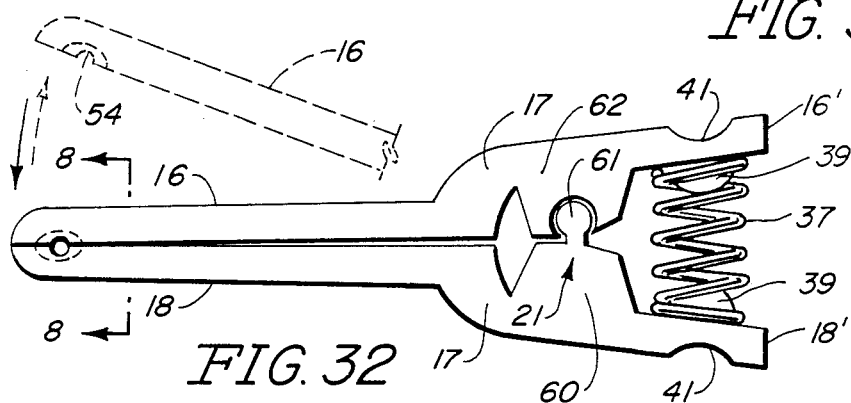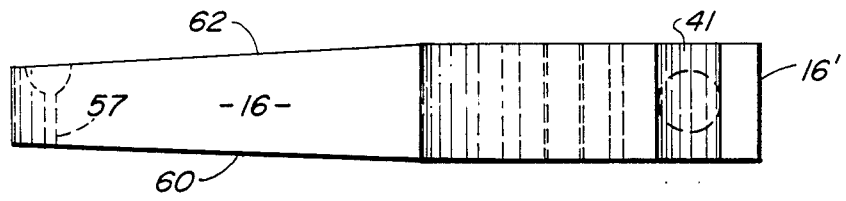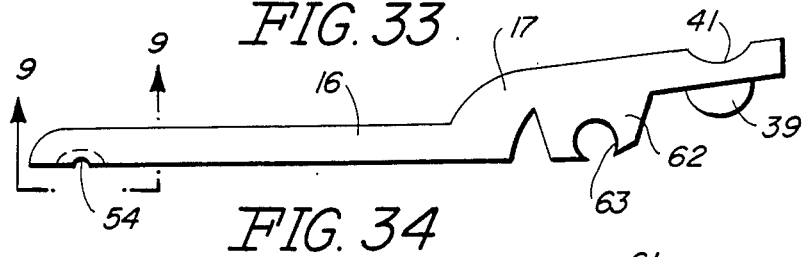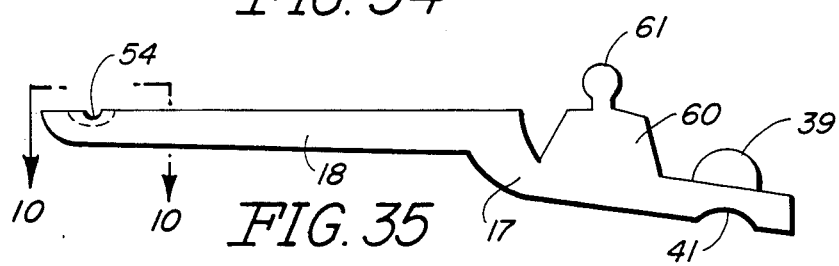

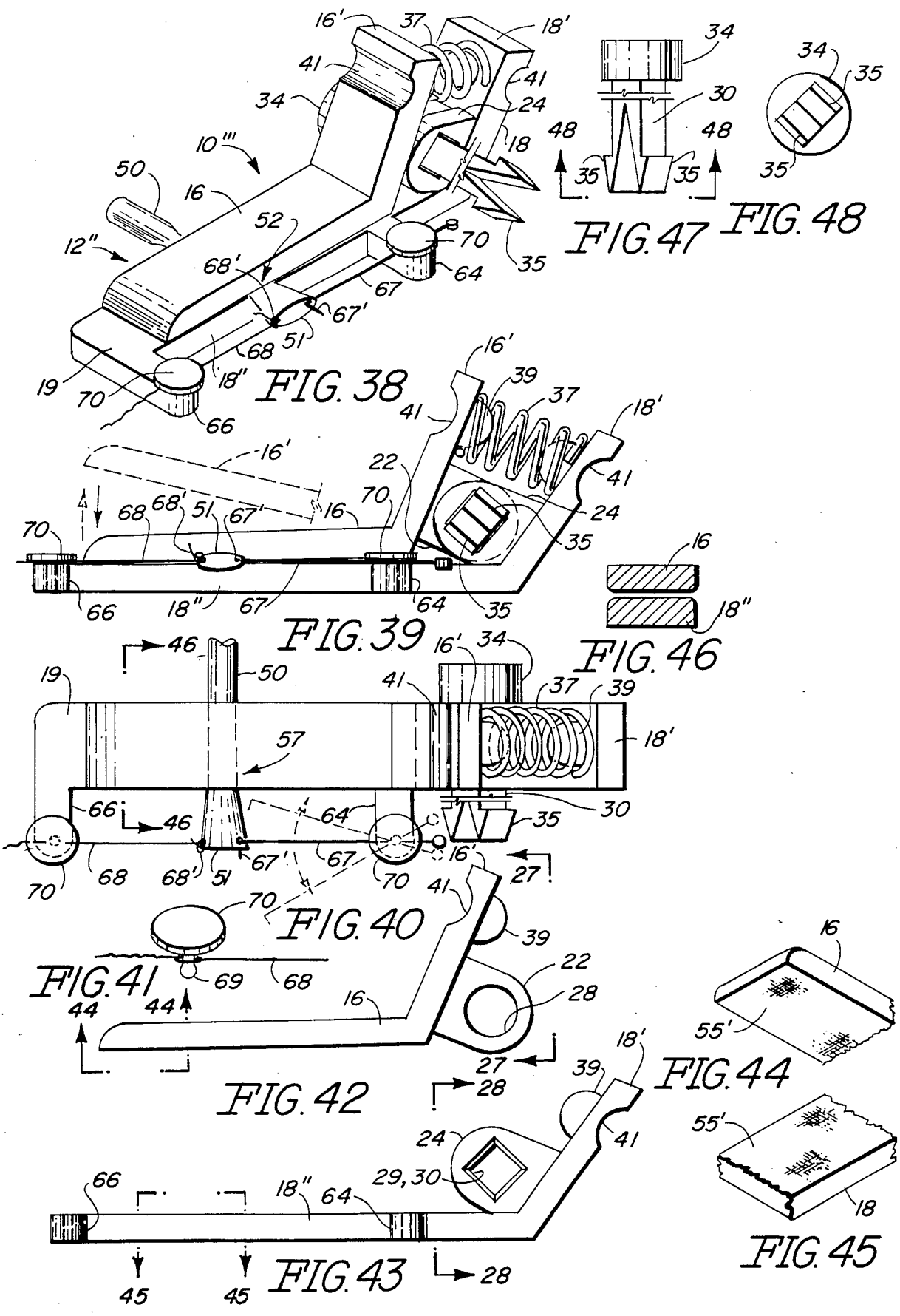

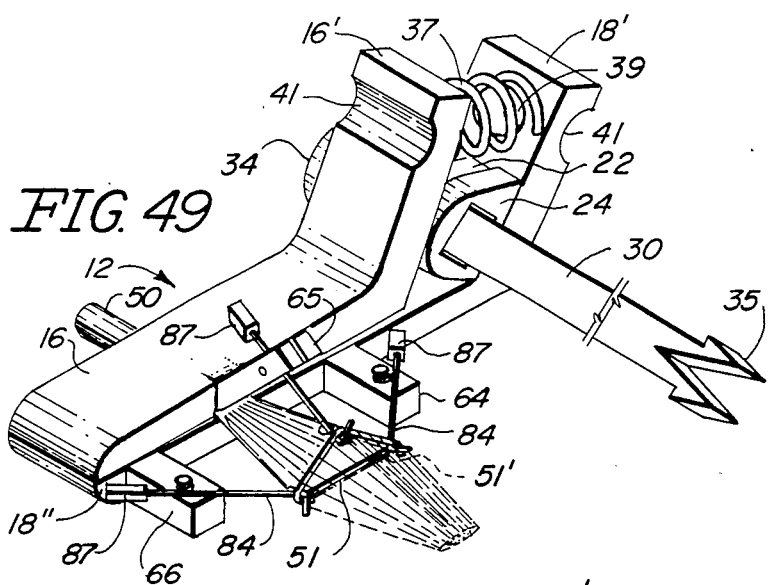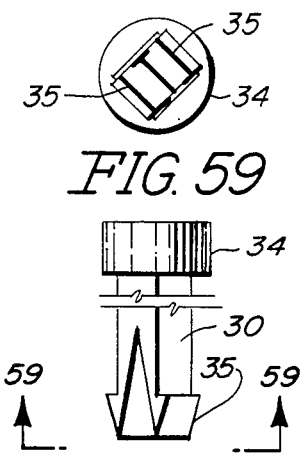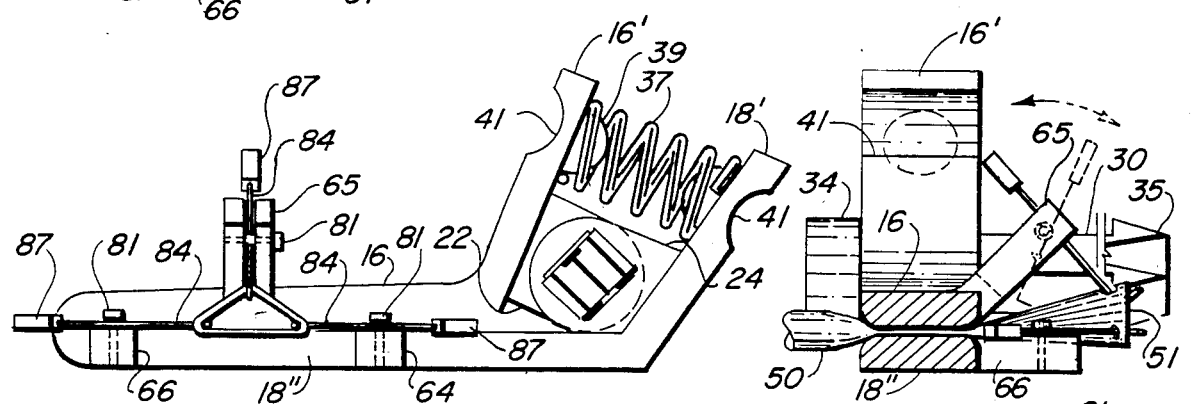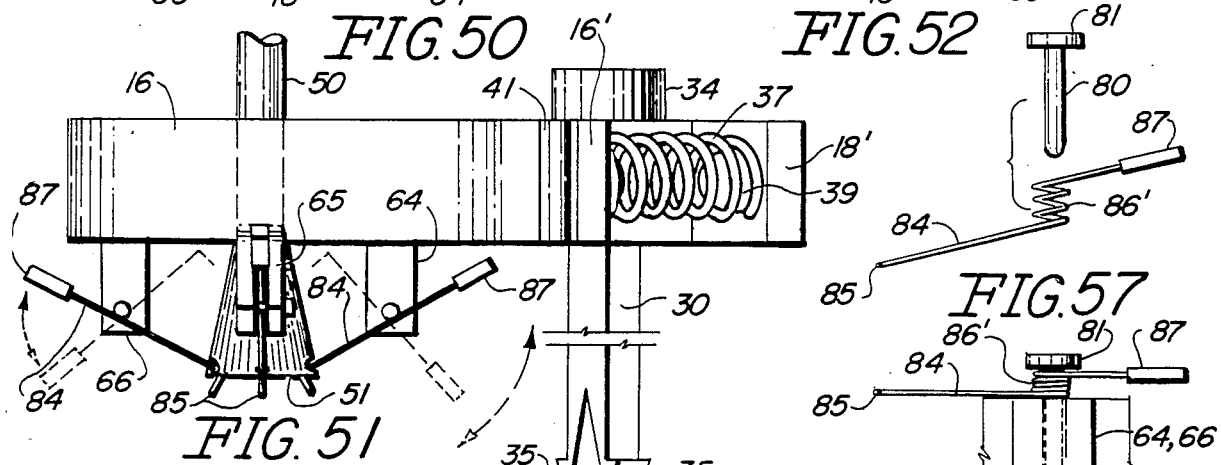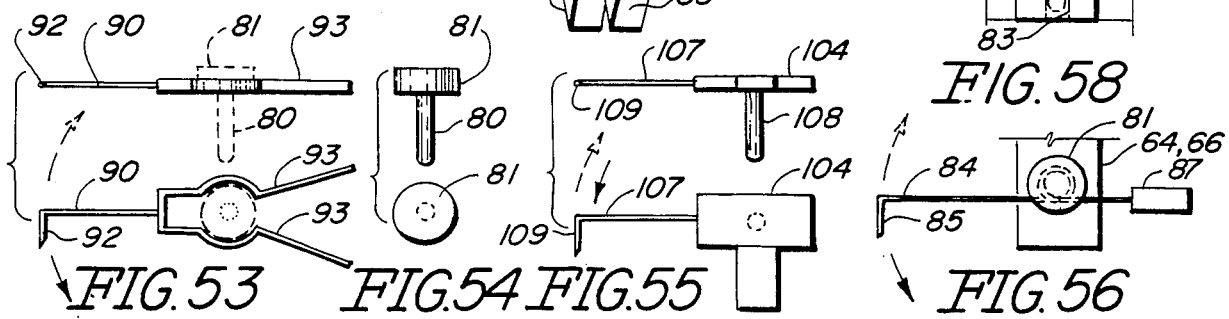

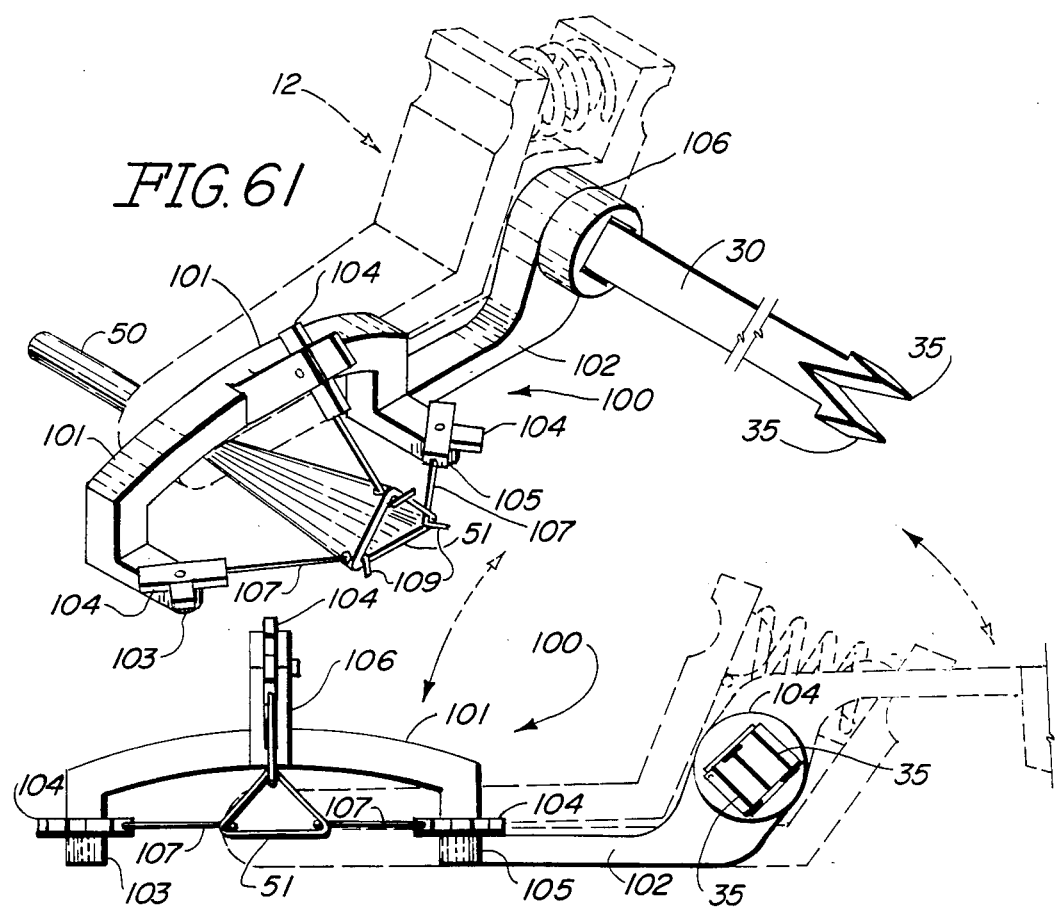
FIG. 61
FIG. 62
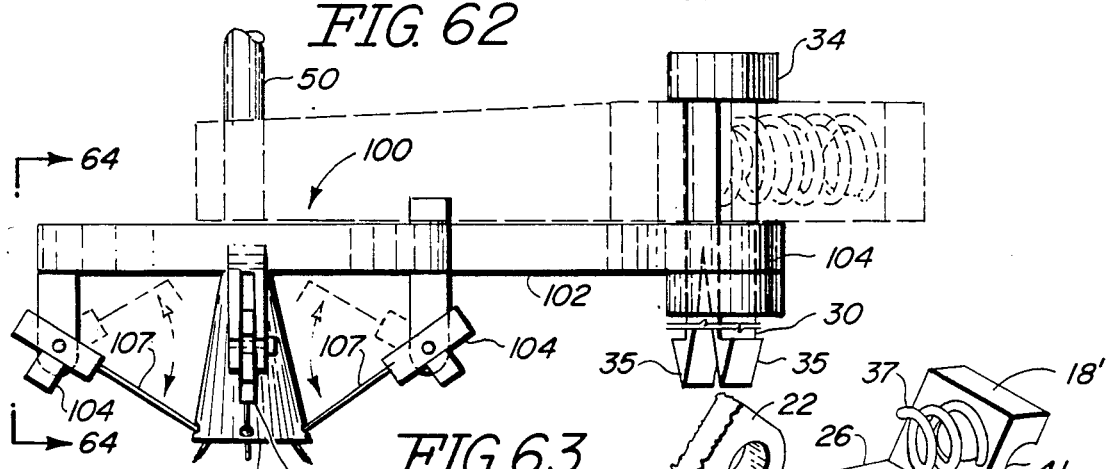
FIG. 63
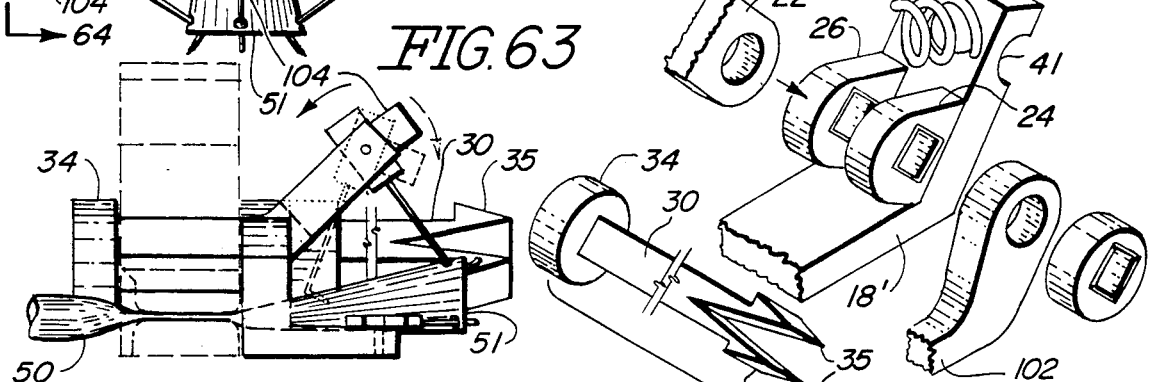
FIG. 64
FIG. 65

1

SURGICAL INSTRUMENTATION FOR BLOOD VESSELS

BACKGROUND OF THE INVENTION

This is a continuation-in-part application of presently copending U.S. Pat. application Ser. No. 791,498, filed Oct. 25, 1985, which is a continuation-in-part of U.S. Pat. application Ser. No. 743,940 filed on June 12, 1985 now U.S. Pat. No. 4,630,608.

FIELD OF THE INVENTION

This invention relates to surgical instrumentation primarily designed to accomplish surgical attachment of blood vessel sections in a manner which assures proper placement and maintenance of the open ends of the vessel sections to be attached in a properly exposed and attachable position for the application of sutures or like connecting facilities.

DESCRIPTION OF THE PRIOR ART

Vascular surgery or surgery involving blood vessels including both veins and arteries is commonly recognized in the medical profession as being extremely maticulous due at least in part to the size of the vessels frequently involved in the surgical procedure. Such difficulty is due in large part also to the fragile nature of the structure of the nature of the blood vessels. Accordingly, instruments including vascular clamps and like structural facilities to maintain or position vessel sections have to be constructed and applied with great precision in order to prevent damage or destruction to portions of the blood vessel being manipulated.

Vascular surgery dealing with the attachment or reconnection of bloo vessel sections is particularly difficult and frequently time-consuming due to the extreme care which must be taken in the location, positioning and maintenance of the vessel sections. More specifically, open ends of separated vessel sections must be disposed in aligned and engaging relation to one another. Further, such open ends must be maintained in attachable position or engagement with one another so as to be properly exposed for suturing by the surgeon or for the process of applying any other connecting means thereto. In order to accomplish such positioning and maintenance of the open ends, many instruments are currently in use in the performing of such surgical techniques are less than totally satisfactory.

One prior art surgical technique associated with the proper positioning and maintenance of vessel sections relative to one another for attachment involves the use of a "bundle" of thread or coils which provides a solid "plug" on which the extremities or ends of the vessel sections are positioned. Suturing then occurs about the extremities to be made while the supporting plug is maintained on the interior of the joined vessel sections. The specific structure of the plug is such as to allow itself to become "unwound" by passing a single portion of the coil or thread through the area being sutured and applying a pulling force thereto. Suturing or closing of the exiting hole for the thread or coil is then accomplished in conventional fashion after the entire "plug" has been removed by its unwinding or unraveling. While apparently applicable for its intended function, the process and apparatus associated with the aforementioned and described prior art techniques may be considered by some to have certain inherent disadvantages associated with the removal of the thread or coil from the interior of the vein after the sutured extremities are almost closed.

Accordingly, there is a recognized need in the medical profession for proper surgical instrumentation particularly designed and constructed for the positioning and maintenance of blood vessel sections and open ends or extremities thereof in an attachable position which is readily exposed for the application of sutures and like connecting means to the open ends thereof.

SUMMARY OF THE INVENTION

The present invention is directed towards surgical instrumentation in the form of a clamp assembly preferably including at least two clamps. Each clamp is defined by two lever arms pivotally interconnected to one another intermediate opposite ends thereof by a fulcrum structure. Each of the arms of a specific clamp structure are cooperatively dimensioned and configured so as to be disposed in a normally closed position through the provision of a biasing means disposed between free ends of the arm. The opposite ends of the arms are structured to include a positioning means specifically configured to engage and maintain blood vessel sections in a preferred orientation relative to one another at the surgical site.

When the clamp assembly comprises two clamps, a securement means in the form of an elongated securement pin is secured to each of the clamps substantially adjacent to or interconnecting with the fulcrum structure of each clamp. The longitudinal dimension of the pin is sufficient to allow sliding movement of each of the clamps along the length of the pin so as to adjust the relative positions of the pins and the spacing in between.

In certain embodiments a single clamp of the structure defined herein is utilized to stop blood flow within the vessel section, ad the need for the aforementioned securement pin is eliminated. The individual arms of the one clamp are structure to include an integrally formed fulcrum structure defining a pivotal connection between the arms defining the one clamp. In this embodiment, the biasing means is appropriately located between the free ends so as to normally bias the clamp in what may be referred to as a closed position.

Common to each of the individual clamps whether used individually or in combination with another clamp is the aforementioned positioning means. In the preferred embodiments of the present invention, the positioning means is integrally formed on the inner surfaces of each lever arm of each clamp. In one embodiment, the positioning means comprises two elongated groove or channel sections integrally formed in the respective inner surfaces wherein the two grooves are disposed in an aligned, coaxial relation to one another so as to define a sleeve in which the blood vessel section is positioned and maintained. The structure of the arms of each clamp is such as to enclose and engage the outer surface of the vessel section while at the same time not causing damage due to crushing of the vessel section.

In another embodiment of the positioning means, the inner surfaces of each clamp is constructed to have a textured surface so as to provide at least a minimal frictional resistance in order to properly grip or engage the outer surface of the vessel section held by an individual clamp.

Another important feature of certain preferred embodiments of the present invention include the provision of an orientation means positioned in cooperative relation with selected clamp structures and adjacent the inner sides thereof. The purpose of the orientation means is to maintain and properly orient the extremity of the vessel section held by the clamp so as to facilitate surgical connection with an extremity of the vessel section held by the next adjacent clamp. The proper orientation is accomplished by a plurality of connecting means removably engaging the extremity of each vessel section. The plurality of connecting means are disposed in a substantially surrounding relation such that the plurality of connecting means engage the extremity at a plurality of locations in spaced relation to one another along the periphery of the extremity to be secured.

The invention accordingly comprises the features of construction, combination of elements and arrangement of parts which will be exemplified in the construction hereinafter set forth, and the scope of the invention will be indicated in the claims.

BRIEF DESCRIPTION OF THE DRAWINGS

For a fuller understanding of the nature of the present invention, reference should be had to the following detailed description taken in connection with the accompanying drawings in which:

FIG. 1 is an isometric view of a preferred embodiment of the clamp assembly of the present invention.

FIG. 2 is a side plan view of the embodiment of FIG. 1 wherein a partially open view of the clamp is represented in cutaway form in phantom lines.

FIG. 3 is a top plan view of the embodiment of FIG. 1.

FIG. 4 is a side plan view of one arm of a clamp structure shown in detail.

FIG. 5 is a side plan view of the other arm of a clamp structure shown in a detail view.

FIG. 6 is an end view of a structure included in the fulcrum structure of the present invention as shown along line 6—6 of FIG. 4.

FIG. 7 is a sectional view along line 7—7 of FIG. 5.

FIG. 8 is a sectional view along line 8—8 of FIG. 3.

FIG. 9 is a perspective view in partial cutaway along line 9—9 of FIG. 4.

FIG. 10 is a perspective view in partial cutaway of the positioning means along line 10—10 of FIG. 5.

FIGS. 11 and 12 are each perspective views in partial cutaway of another embodiment of the positioning means of the present invention differing from the embodiments of FIGS. 9 and 10.

FIG. 13 is a front plan view of a securement pin interconnecting the fulcrum structures of adjacent clamps.

FIG. 14 is an end view along line 14—14 of FIG. 13.

FIG. 15 is a perspective view of another preferred embodiment of the clamp assembly of the present invention.

FIG. 16 is a side plan view of the embodiment of FIG. 15 wherein a partially open position is represented in phantom lines in partial cutaway.

FIG. 17 is a top plan view of the embodiment of FIG. 16.

FIG. 18 is a side plan view in detail of one arm of the clamp structure of FIG. 15.

FIG. 19 is a side plan view in detail of the other arm of the clamp assembly of FIG. 15.

FIG. 20 is a front plan view of the fulcrum pin associated with the clamp of FIG. 15.

FIG. 21 is an end view along line 21—21 of FIG. 20.

FIG. 21A is a sectional view.

FIG. 21B is a detailed view in partial cutaway of the positioning structure associated with the embodiment of FIG. 15.

FIG. 21C is a detailed view in partial cutaway similar to the embodiment of FIG. 21B.

FIG. 22 is a perspective view of another embodiment of the clamp assembly of the present invention.

FIG. 23 is a side plan view of the embodiment of FIG. 22.

FIG. 24 is a top plan view of the embodiment of FIG. 22 showing the engagement of a blood vessel section in partial cutaway.

FIG. 25 is a side plan view of one arm of the clamp of FIG. 22 shown in detail.

FIG. 26 is a side plan view of the other arm of the clamp of FIG. 22 shown in detail.

FIG. 27 is a bottom view in partial cutaway along line 27—27 of FIG. 25.

FIG. 28 is a top view along line 28—28 of FIG. 26.

FIG. 28A is a side view in partial cutaway of details of a tweezer or like tool structure adapted to fit within and activate to an open position the embodiment of FIG. 22.

FIG. 29 is a front plan view of the securement pin used in combination with the clamp assembly embodiment of FIG. 22.

FIG. 30 is an end view along line 30—30 of FIG. 29.

FIG. 31 is an isometric view of yet another embodiment of the clamp assembly of the present invention.

FIG. 32 is a side plan view of the embodiment of FIG. 31.

FIG. 33 is a top plan view of the embodiment of FIG. 31.

FIG. 34 is a side plan view of one arm of the clamp of FIG. 32 shown in detail.

FIG. 35 is a side plan view of the other arm of the embodiment of the clamp structure as shown in FIG. 31 in detail.

FIG. 36 is a detailed view in partial cutaway of a portion of the fulcrum structure of the present invention.

FIG. 37 is a detailed view in partial cutaway of a cooperating portion of the fulcrum structure used in the clamp structure of FIG. 31 and in cooperative movable relation with the structure of FIG. 36 to form a pivotal connection between the arms as shown in FIGS. 34 and 35.

FIG. 38 is a perspective view of yet another embodiment of a clamp assembly of the present invention incorporating an orientation structure for the end or extremity of a vessel section.

FIG. 39 is a side plan view of the embodiment of FIG. 38 wherein a partially open position is indicated in phantom lines.

FIG. 40 is a top plan view of the embodiment of FIG. 38.

FIG. 41 is a detailed view of a connecting structure used in combination with the embodiment of the clamp as shown in FIG. 38.

FIG. 42 is a side plan view of one of the arms of the clamp of FIG. 38 shown in detail.

FIG. 43 is a side plan view of the other arm of the clamp of FIG. 38 shown in detail.

FIG. 44 is a detailed view taken along line 44—44 of FIG. 42 shown in partial cutaway.

FIG. 45 is a detailed view in partial cutaway taken along line 45—45 of FIG. 43.

FIG. 46 is a sectional view taken along line 46—46 of FIG. 40.

FIG. 47 is a front plan view of the fulcrum pin associated with the clamp assembly of the embodiment of FIG. 38.

FIG. 48 is an end view taken along line 48—48 of FIG. 47.

FIG. 49 is a perspective view of another embodiment of the clamp assembly of the present invention with an orienting structure for the vessel section being engaged by the clamp.

FIG. 50 is a side plan view of the embodiment of FIG. 49.

FIG. 51 is a top plan view of the embodiment of FIG. 50.

FIG. 52 is an end view of the embodiment of FIG. 50.

FIG. 53 is a combined side view and top plan view of a connecting structure associated with the embodiment of FIG. 38.

FIG. 54 is a side view and top plan view associated with the embodiment of FIG. 38.

FIG. 55 is a combined side view and top plan view associated with the embodiment of FIG. 51.

FIG. 56 is a top plan view of another embodiment of a connecting structure associated with the embodiment of FIG. 51.

FIG. 57 is an exploded view in detail of the components of the connecting structure associated with the embodiment of FIG. 51.

FIG. 58 is a side view in partial cutaway of the embodiment of FIG. 57 mounted on the clamp structure as shown in FIGS. 50 and 51.

FIG. 59 is an end view along line 59—59 of FIG. 50.

FIG. 60 is a front plan view of the fulcrum pin associated with the clamp structure as shown in the embodiment of FIG. 49.

FIG. 62 is yet another embodiment of the orienting structure and accompanying connecting structure to properly orient the extremity or end of the vessel structure as shown in FIG. 61 in perspective.

FIG. 62 is a side plan view of the embodiment of FIG. 61.

FIG. 63 is a top plan view of the embodiment of FIG. 61.

FIG. 64 is an end view of the embodiment of FIG. 63 taken along line 64—64.

FIG. 65 is an exploded view of the fulcrum structure of a clamp assembly in partial cutaway showing the connection of the embodiment of the orientation structure as shown in FIG. 6.

Like reference numerals refer to like parts throughout the several views of the drawings.

DETAILED DESCRIPTION OF THE PREFERRED EMBODIMENT

Figure 66:
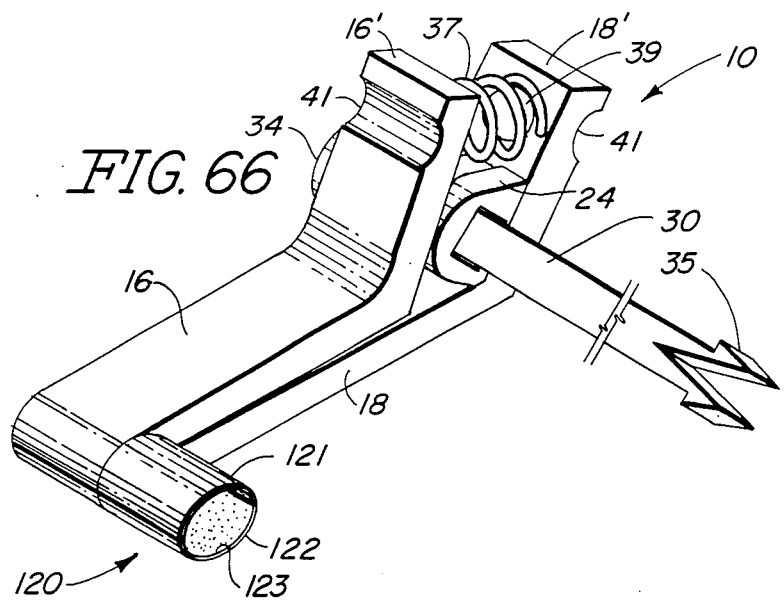
FIG. 66 is yet another embodiment of the clamp assembly of the present invention.

The present invention is directed towards surgical instrumentation of the type specifically designed to facilitate the joining of vessel segments of blood vessels. In one preferred embodiment, the invention includes the clamp assembly generally indicated as 10 including a plurality, and preferably two clamps 12 and 14, wherein each of the clamps are identically structured and dimensioned. With reference primarily to FIGS. 1 through 5, each of the clamps include two lever arms 16 and 18 pivotally interconnected to one another by a fulcrum structure generally indicated as 20. The fulcrum structure includes a plurality of outwardly extending fingers 22, 24, 26 (see FIGS. 4 through 7) wherein each of the fingers are designed to be positioned in a mating, aligned relation to one another such that finger 22 fits within the space 25 between fingers 24 and 26. Each of the fingers include an aperture 28 and 29, 30 which are disposed in coaxial relation to one another when the fingers are in the aligned position such that finger 22 is in space 25 between fingers 24 and 26. A securement means preferably in the form of an elongated pin 30 is dimensioned to pass through the fulcrum structure including the apertures in each of the fingers 22, 24 and 26 of each adjacently positioned clamp 12 and 14 (see FIGS. 1 through 3). By virtue of the interconnection of the pin 30 to each of the fulcrum structures of the clamps 12 and 14, these clamps are maintained in a preferred spaced apart location to one another and at a distance to facilitate the connection of vessel sections, to be described in greater detail hereinafter. It should be emphasized that the longitudinal dimension of the pin 30 is sufficient to allow selective positioning of each of the clamps 12 and 14 relative to one another along the length of the pin 30. This therefore allows the regulation of the size of space 32 (see FIG. 3) between the clamps 12 and 14 as indicated by the directional arrow 33.

The pin 30 further includes a somewhat enlarged head portion 34 and an inherently biased opposite end including two spaced apart members 35. In the position shown in FIGS. 13 and 14, the members 35 are spaced apart from one another a distance sufficient to prevent passage of the members 35 through the apertures 28, 29, 30 of the individual fingers 22, 26 and 24 respectively. However, due to the material from which the pin 30 is formed, the ends 35 may be forced together to reduce the overall transverse dimension thereof thereby allowing passage of these members 35 through the apertures as mentioned above. The proper positioning therefore of the pin 30 is best shown in FIGS. 1 and 3. Due to the inherent biasing of the members 35, they will naturally be forced outwardly by a snap action type movement thereby serving as a locking member to prevent inadvertent removal of the pin 30 from the fulcrum structures 20. It should further be noted that the apertures 29, 30 in fingers 26 and 24 are configured to correspond to the external, peripheral configuration of the pin 30. Both the periphery of the apertures 29, 30 are multisided as well as the periphery of the external surface of the pin 30. Relative motion therebetween is thereby prevented. However, the periphery of the aperture 28 of finger 22 is not correspondingly configured but to the contrary has a circular configuration of sufficient dimension to allow relative rotation of the finger 22 and attached arm 16 about the pin 30. The longitudinal axis of the pin 30 thereby defines the pivotal axis of the clamp as the arm 16 is movable relative to the arm 18 upon a depression or pressure being applied to the free ends 16' and 18' towards one another. A biasing spring 37 is mounted between each of the free ends 16' and 18' of each clamp 12 and 14 and secured in the position shown in FIGS. 1 and 2 by outwardly extending nipples 39. By virtue of the placement and structure of the biasing spring 37, it should be readily apparent that each of the clamps are normally biased in what may be considered a closed position as shown in FIGS. 1 and 2. Pressure being exerted against the free end 16' and 18' causes rotation or pivotal movement of the one arm 16 relative to the other arm 18 as shown in phantom lines in FIG. 2.

Due to the extremely small size of such clamps, the opening and closing thereof is accomplished through the manipulation of the free ends 16' and 18' of the clamps by means of an instrument 43 of the type generally shown in FIG. 28A. Therefore, indentations 41 are elongated and integrally formed in each of the free ends along the exterior surface thereof as clearly shown. These indentations are specifically sized to receive appropriate correspondingly configured portions of a tool or instrument. Another embodiment of the present invention as shown in FIGS. 15–28A includes the free ends 16' and 18' each having an indentation 41' with a substantially hemi-spherical or concave configuration rather than the elongated configuration as shown in a majority of the embodiments of the Figures shown herein. Accordingly, the tool generally in the form of tweezers or like instruments have appropriately shaped projections 41'' so as to fit into the concave or spherical indentations 41'. Accordingly, the corresponding configurations of the indentation 41' and projections 41'' on the tweezer like tool 43 enables the tweezers to approach the free ends, from the rear of the clamp assembly as at 14' in any of a number of varying angular approaches rather than in a straight, in-line approach from the rear.

Another feature of the present invention is the inclusion of positioning means generally indicated in FIG. 1 as 52 for the gripping and maintenance of blood vessel sections 50 to be connected to one another. More specifically, the positioning means 52 in the embodiment of FIG. 1 includes two different sizes of positioning means 52 and 52' wherein each positioning means includes an integrally formed groove 54 (see FIGS. 9 and 10) formed in the inner surface 55 of each of the arms 16 and 18. It should be emphasized that a greater number than two positioning means may be formed on a given clamp structure and only the two positioning means 52 and 52' are shown for purposes of clarity. The inner side of each groove 54 has an outwardly extending flared portion 56. The inner side of each groove is defined by the side facing the adjacent clamp and out of which the open or free extremity or end of the vessel section 50 extends. When the two arms 16 and 18 are disposed in the position as shown in FIGS. 1, 2 and 3, the grooves 54 are disposed in coaxial, aligned relation to one another as well as the outwardly flared portion 56. This thereby defines a sleeve which is dimensioned and configured to effectively surround the vessel section 50 and engage the vessel sections outer surface to the extent of maintaining the position of the vessel section as best shown in FIGS. 38, 40, 49, 50, and 51 directed to additional embodiments of the present invention. The sleeves 57 are made up of the groove or channel portions 54, 56 integrally formed in the inner surface 55 of each of the arms 16 and 18. Also, two positioning means 52 and 52' are formed merely to add a versatility to the clamp assembly 10 providing positioning means of varying sizes to accommodate blood vessels of varying sizes.

With reference to FIG. 8, it should be emphasized that the longitudinal edges 59 are rounded rather than straight so as to prevent damage to the vessel sections 50 when gripped in the positioning means 52 or 52'.

With regard to FIGS. 11 and 12, another embodiment of the positioning means is the absence of any grooves 54 or accompanying flared portions 56 but merely the forming of the inner surfaces 55' to have a texture or possibly mild roughened or knurled configuration so as to provide at least a minimal amount of friction to the vessel sections 50 when engaged therebetween.

The embodiment shown in FIGS. 15 through 21 is similar to the embodiment of FIGS. 1 through 14 with the exception that a single positioning means 52 is formed comprising sleeve 57 defined by integrally formed elongated grooves 54 having a straight line configuration absent any flared portion at the inner ends thereof as shown in FIG. 1. In addition, it should be noted that the fulcrum pin 30 may be of a varying but elongated configuration of sufficient longitudinal dimension to allow mounting of an additional clamp 10' in adjacent, side-by-side relation to the clamp shown in FIG. 13. Further, the clamps may be varied towards or away from one another so that the space therebetween 32 (see FIG. 3) may be varied to perfect the proper positioning of the extremity 51 of vessel section 50 (see FIGS. 38 and 49).

Another feature of the present invention with primary reference to FIGS. 3 and 17 is the provision of a substantially straight line longitudinal side 60 defining the outer side of each clamp 12. However, the inner side 62 has a somewhat convergent orientation from a point intermediate the ends as at 63 to the extremity 65 substantially adjacent the positioning means 52. This convergent orientation 62 is to again allow for sufficient space 32 to accomplish manipulation and surgical attachment of the extremities 51 of the vessel sections 50.

With regard to the embodiment of FIGS. 22 through 30, the configuration of the clamp 14' particularly relating to the ends as at 16' and 18' and the intermediate section 17 of each of the arms 16 and 18 is the primary difference in this embodiment from the remainder of the embodiments of the subject invention. It should be noted that with regard to the embodiments of FIGS. 1 through 21, the individual clamps 12 or 14 have a somewhat upwardly angled orientation of the free ends from a point of approximately just before the fulcrum structure. However, in the embodiment of FIGS. 22 through 28, each of the arms has a substantially in-line configuration wherein the free ends 16' and 18' are not angled upwardly. The remaining portions of this clamp are substantially the same including the positioning means 52, fulcrum structure 20, fulcrum pin 30 and biasing means and outwardly extending nipples 37 and 39 respectively.

With regard to the embodiments of FIGS. 31 through 37, a clamp assembly 10'' includes a single clamp 13 which is not designed to be interconnected by a fulcrum pin 30 defining a securement means as in the embodiments described above. To the contrary, the clamp 13 is designed to be used for the gripping of vessel sections and properly positioning them in cooperative position relative to the type of clamp as shown in FIGS. 49 and/or 61 as described in grater detail hereinafter. The positioning means 52, biasing means 37, indentations 41, intermediate portion 17 of arms 16 and 18 are the same with regard to the embodiment of FIGS. 22 through 28. However, the difference is that the fulcrum structure generally indicated as 20' includes an integrally formed base 60 on arm 18 adjacent the intermediate portion 17 including an integrally formed upwardly extending elongated tongue member 61 dimensioned and configured to be received within the base 62 by means of elongated sockets 63 which are both integrally formed in the intermediate section 17 of the arm 16. It can readily be seen that the pivotal connection 20' or fulcrum structure serves to allow pivotal movement and separation of the arms 16 and 18 so that the grooves 54 of the positioning means 52 can separate and be readily placed in surrounding engagement to a vessel section 50 (not shown for purposes of clarity). Another important feature of the embodiment of FIGS. 31 through 37 is the integral formation of the components 61 and 63 of the fulcrum structure 20' being integrally formed and therefore inexpensive to produce.

With regard to the embodiments of FIGS. 38 through 48, the clamp assembly 10''' includes one or more clamps 12'' comprising an arm 16 similar to the remainder of the embodiments described above and a modified arm 18' having an orientation means mounted at least partially thereon. The orientation means includes a plurality of outwardly extending posts 64 and 66 integrally secured to the arm 18'' wherein the longitudinal dimension as at 19 extends outwardly from the corresponding end of the arm 16. The posts 66 and 64 are disposed on opposite sides of the positioning means 52 and more specifically the inner side thereof from which the extremity 51 of vessel section 50 projects. Each of the posts 64 and 66 includes a connecting means in the form of a connecting element or structure 67 or 68. Connector 67 is formed from a wire or like material which may have inherent flexibiltiy and a hook or like member 67' fixed to the outer extremity thereof. The element 67 may be wound around base 69 of a button-like mounting member 70. Alternately, the extremity 51 of vessel section 50 may be maintained in place in cooperation with the connector 67 by a second embodiment of the connector 68. This may be in the form of a thread-like member sutured or otherwise secured as at 68' to the extremity 51 of the vessel 50 and, as shown in FIG. 41, wrapped around the base 69 of the button-like mounting member 70. As shown in FIG. 38, the extremity 51 is thereby opened and extended so as to facilitate suturing or otherwise connecting to a similarly disposed and opened extremity from what may be mounted on or engaged by an adjacent clamp (not shown for purposes of clarity).

With regard to the embodiments of FIGS. 49 through 52, the orientation means of the present invention comprises in addition to posts 64 and 66 integrally formed on arm 18'' on opposite sides of the positioning means, a third post 65 integrally formed to extend outwardly from a common side of arm 16 relative to the posts 64 and 66 but between posts 64 and 66 and substantially angularly outwardly therefrom and above. The extremity 51 is engaged at a plurality of spaced apart locations to further extend the extremity 51 in an outwardly flared position to facilitate connection to an extremity of an adjacently positioned vessel section when an additional clamp 14 (not shown) is positioned adjacent thereto and on the pin 30 as explained with regard to the embodiment of FIG. 1.

A variety of connecting means may be utilized. With regard to the embodiments of FIGS. 57 and 58, similar connections are employed in the connecting means represented in FIG. 49. More specifically, a needle or nail-like element, of minute proportions, 80, having a button-like top 81 is anchored within an aperture or channel 83 of each of the posts 64 and 66. These serve to mount or anchor connectors 84 having hook-like ends 85 and minute handles or positioning members 87.

Modifications of the connecting means are shown in FIGS. 53 through 55 and include a spring lock connector having spaced apart inherently biased legs 93 and a hook-like extremity for engagement of the end 51 of the section 50 as at 92.

With regard to FIG. 55, the connecting means shown therein is specifically adapted to be used with regard to the additional embodiment of the orienting means generally indicated as 100 in FIG. 61. In the embodiments of FIGS. 61 through 65, the orientation means 100 includes a base 101 having a substantially arcuate configuration and integrally secured to a supporting and positioning arm 102 which has an apertured head portion 106 designed to surround and be supported by the pin 30 (see FIG. 65). As can be seen with regard to FIG. 61, the orientation means 100 is designed to be positioned selectively into and out of immediately adjacent relation to the clamp 12 or more specifically, the inner side thereof. The extremity 51 is thereby properly presented relative to a similarly positioned extremity (not shown) on an adjacently positioned clamp 14 (not shown) which would also be mounted on the pin 30 having sufficient length to accommodate two spaced apart but adjacent clamps 12 and 14 and two spaced apart but cooperatively positioned orientation means 100.

The base 101 has integrally formed thereon outwardly extending posts 103 and 105 at essentially opposite ends thereof. In addition, a third post 116 extends intermediate the posts 103 and 105 and is angled to extend outwardly therefrom and above the posts 103 and 105. Each of the posts 103, 105, and 116 include a connecting means shown in detail in FIG. 55. The connecting means includes a connector base 104 pivotally mounted on the respective posts by a fixed pivot and anchor pin 108 which fit within appropriately positioned sockets or channels formed in the respective posts 103, 105, and 116.

Accordingly, the extremity 51 of the vessel section 50 is contacted at a plurality of spaced apart locations by the individual connectors 107 having hooks or like gripping extremities 109. However, it is important to note both with regard to the embodiment shown in FIG. 49 and 61 that the extremity 51 of the vessel section extends outwardly beyond the respective posts and the respective individual connectors 107 are angled outwardly to engage the extremity 51 at a plurality of locations. The outward extension of the extremity 51 beyond the outward extension of the post is for purposes of accomplishing clear access to the extremity of the vessel section as when using a laser or other instrumentation which requires direct access without obstruction by any of the posts or respective connectors.

As previously stated, the embodiments of the clamp structure as shown in FIGS. 31 through 37 includes a single clamp 13 which is primarily designed for clamping of the blood vessel at any location in the general surgical site. Accordingly, while other embodiments of the clamp assembly shown herein may be used in combination with one another, the individual clamp 13 may be used at the surgical site for the purposes of stopping blood flow.

Figure 67:
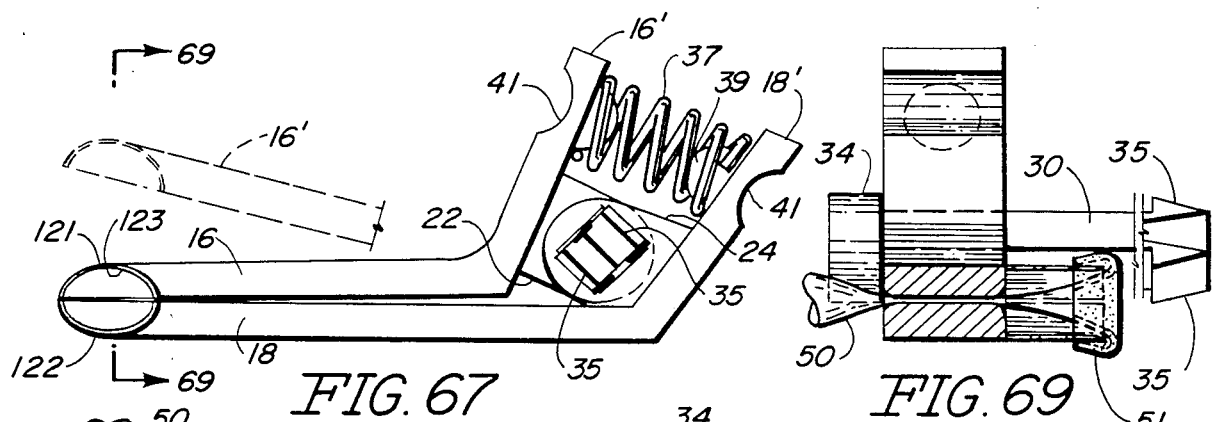
FIG. 67 is a side plan view of the embodiment of FIG. 66.
Figure 69:
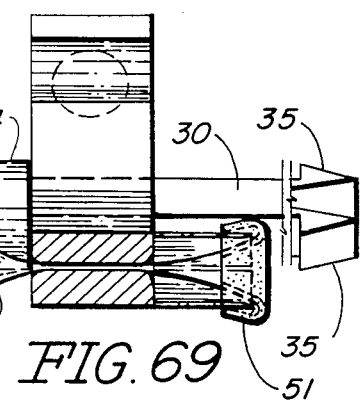
FIG. 69 is a sectional view along line 69—69 of FIG. 67.
Figure 68:
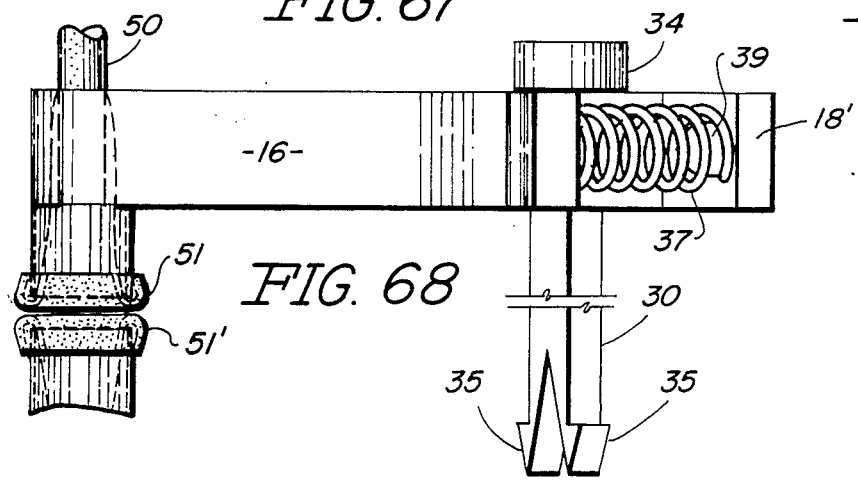
FIG. 68 is a top plan view of the embodiment of FIG. 67.

In the embodiments of FIGS. 66 through 68 yet another embodiment of the clamp assembly 10 includes the same structure with regard to the clamp structure of FIG. 1 with the exception of the orientation means generally indicated as 120 comprising two semi-circular shell extensions 121 and 122 extending outwardly from a flat textured inner surface positioning means so as to hold and maintain the extremity 51 of the vessel section 50 as shown in FIG. 68. However, the embodiment of FIGS. 66 through 69 differ from the remainder of the embodiments of the present invention by folding back the extremity 151 over the peripheral edge 123 of the mating shells 121 and 122. The extremity 151 is thereby adequately maintained in a position for connection to an adjacently positioned extremity of an adjacently positioned section.

It is therefore to be understood that the following claims are intended to cover all of the generic and specific features of the invention herein described, and all statements of the scope of the invention which as a matter of language, might be said to fall therebetween.

Now that the invention has been described, What is claimed is:

1. A surgical instrumentation assembly of the type primarily designed for the positioning of open ends of blood vessel sections in aligned relation to one another, said assembly comprising:
   (a) a clamp assembly including at least one clamp each comprising two substantially elongated arms movably secured to one another,
   (b) a fulcrum structure mounted on said one clamp and disposed intermediate opposite ends of said two arms and interconnected thereto and structured to define a pivotal connection between said two arms,
   (c) said one clamp structured to include a positioning means at least partially mounted on each of said two arms adjacent a first of said opposite ends thereof and structured for holding and positioning a vessel section,
   (d) said positioning means of each clamp including at least one gripping structure defined by a gripping surface integrally formed on an inner surface of each arm, said gripping surfaces of each clamp disposed in aligned relation to one another and cooperatively configured to engage an exterior surface of the respective blood vessel sections associated with each clamp,
   (e) securement means interconnected between two of said clamps and disposed and structured for placement of said two clamps in spaced, adjacent and communicating relation to one another,
   (f) said positioning means of said one clamp structured and disposed in substantially aligned relation to one another of said clamps when interconnected by said securement means and said gripping surfaces of each clamp structure terminating in an outer end and an inner end disposed on opposite longitudinal sides of said respective clamp structure, and
   (h) whereby open attachable ends of the vessel sections on each one clamp are oriented to extend outwardly from said inner end of each positioning means into engageable relation with one another.

2. An assembly as in claim 1 wherein said gripping structure of each clamp comprises a sleeve integrally formed in said respective clamps, said sleeve defined by said two gripping surfaces, each including an elongated groove formed in each of said arms.

3. An assembly as in claim 2 wherein said sleeve of each clamp extends transversely between opposite longitudinal sides of said clamp and is open at opposite ends thereof to define an open inner end and an open outer end.

4. An assembly as in claim 3 wherein said open inner end of each sleeve comprises a substantially flared, enlarged configuration relative to said outer end of each sleeve and a portion of the remainder of the length thereof.

5. An assembly as in claim 2 wherein each of said gripping surfaces includes a textured finish thereon, said textured finish structured to provide at least a minimal frictional resistance to an engaged vessel section.

6. An assembly as in claim 1 wherein said gripping surfaces of each gripping structure has a substantially planar configuration disposed in coplanar relation with said inner surface of a respective one of said arms on which it is formed.

7. An assembly as in claim 6 wherein each of said gripping surfaces includes a textured finish thereon, said textured finish structured to provide at least a minimal frictional resistance to an engaged vessel section.

8. An assembly as in claim 7 wherein said positioning means of each clamp comprises a plurality of gripping structures disposed in spaced, parallel relation to one another and at least two of said plurality of gripping structures having cross-sectional dimensions which differ.

9. An assembly as in claim 1 wherein said clamp comprises a second of said opposite ends being disposed and substantially defining an opposite end of said clamp relative to said positioning means, said second ends being movably disposed in spaced relation to one another, said second ends selectively positionable towards one another upon pressure being applied thereto, said two arms pivotally connected to one another for movement of opposite ends of said clamp about said fulcrum structure.

10. An assembly as in claim 9 wherein each of said second ends include an indentation portion formed on an outer surface thereof, said indentation portions cooperatively disposed and configured to receive a tool structure therein, the tool structure designed for positioning of said two ends toward one another upon being pressed together and the resultant positioning means of said clamp being disposed away from one another.

11. An assembly as in claim 10 wherein said indentation portions include a substantially concave and hemispherical configuration.

12. An assembly as in claim 11 wherein said tool comprises projections correspondingly configured to said indentation portions and respectively disposed so as to concurrently engage said indentation portions.

13. An assembly as in claim 1 further comprising biasing means mounted on each of said clamps between said second ends of said arms and disposed and structured for biasing said second ends away from one another and biasing said first ends towards one another.

14. An assembly as in claim 13 wherein said fulcrum structure is disposed intermediate opposite ends of said clamp and said fulcrum structure of each clamp disposed in aligned substantially coaxial relation to one another.

15. An assembly as in claim 11 wherein said securement means comprises an elongated pin of sufficient longitudinal dimension for securement of a plurality of clamps thereto, said clamps connected to said pin in aligned, spaced relation to one another, said clamps movable towards and away from one another along the length of said pin for selective positioning thereof relative to one another.

16. An assembly as in claim 15 wherein said pin is disposed in interconnected relation to said fulcrum structure of adjacently positioned clamps and being disposed and structured to at least partially define a pivotal axis of each of said fulcrum structures.

17. An assembly as in claim 1 wherein said securement means comprises an elongated pin having a sufficient longitudinal dimension for movable attachment to each of said plurality of adjacently positioned clamps, said pin structured for interconnection to said fulcrum structure of said plurality of clamps, said fulcrum structure of each clamp movably disposed in substantially aligned relation to one another.

18. An assembly as in claim 17 wherein said fulcrum structure comprises a plurality of fingers secured to and extending outwardly from cooperative portions of said arms at one end of said clamp opposite to said positioning means, each arm having at least one finger secured thereto and said plurality of fingers disposed in adjacent, substantially aligned relation to one another, each of said plurality of fingers of each of said plurality of clamps movably secured to said pin.

19. An assembly as in claim 18 wherein each of said plurality of fingers comprise an aperture formed therein and dimensioned at least in part to allow passage therethrough of said pin, said pin and said apertures cooperatively dimensioned and configured to allow pivotal movement of said arms relative to one another and longitudinal movement of said plurality of adjacent clamps along the length of said pin.

20. An assembly as in claim 19 wherein said apertures of said fingers secured to a first of said arms comprise a peripheral configuration corresponding to an exterior surface configuration of said pin, whereby relative rotation is prevented therebetween; said aperture of said fingers secured to a second of said arms comprising a peripheral configuration differing from said exterior surface of said pin, whereby relative rotation is allowed therebetween.

21. An assembly as in claim 20 wherein said exterior surface of said pin is multi-sided.

22. An assembly as in claim 21 wherein said peripheral configuration of said apertures of said other fingers is circular.

23. An assembly as in claim 19 wherein said pin comprises a head portion secured to one end thereof and having a transverse dimension sufficient to prevent passage thereof through said apertures.

24. An assembly as in claim 23 further comprising a locking portion secured to one end of said pin and structured for selective placement between a normal size and a reduced size position for passage through said aperture and maintenance in attached relation to said fulcrum structure.

25. An assembly as in claim 1 further comprising orientation means secured to at least one of said clamps for maintaining a preferred orientation of an end portion of the vessel section engaged by said one clamp, said orientation means extending outwardly from one side of said clamp and including connecting means for attachment to the end portion protruding from said positioning means of said one clamp.

26. An assembly as in claim 25 wherein said orientation means comprises a plurality of posts secured to said clamp and including at least two of said posts disposed in spaced relation to one another on opposite sides of said positioning means and the end portion of the vessel section extending therefrom, said connecting means secured to said post and positionable relative thereto into retaining engagement with the end portio of the vessel section.

27. An assembly as in claim 26 wherein said connecting means comprises a plurality of connections at least equal in number to said posts and extending outwardly from respective ones of said posts into attachment with the end portions of said vessel sections, said plurality of connectors engaging the end portions at a plurality of spaced locations about the end portions.

28. An assembly as in claim 27 wherein at least one of said connectors comprises an elongated, semi-rigid and flexible element movably mounted and selectively positionable into and out of engagement with the end portion of the vessel section.

29. An assembly as in claim 26 wherein at least two of said plurality of posts are secured to a common longitudinal side of one arm of said clamp and extending outwardly therefrom in substantially parallel relation to one another on opposite sides of the positioning means.

30. An assembly as in claim 27 wherein at least one of said connectors comprises a thread of flexible material having one end secured to the end portion of the clamp and being secured to one of said posts and a spaced distance from the end portion.

31. An assembly as in claim 26 wherein said plurality of posts comprise at least a third post secured to said clamp substantially between said two posts and including said connecting means connected thereto and extending outwardly therefrom into attachment with the end portion.

32. An assembly as in claim 31 wherein said connecting means comprises a plurality of connectors at least equal in number to said posts and extending outwardly from respective ones of said posts into attachment with the end portions of the vessel section, said plurality of connectors engaging the end portion at a plurality of spaced locations about the end portion.

33. An assembly as in claim 31 wherein at least two of said plurality of posts are secured to a common longitudinal side of one arm of said clamp and extend outwardly therefrom in substantially parallel relation to one another on opposite sides of the positioning means, said third post secured to a longitudinal side of the other of said two arms of said clamp relative to said two posts.

34. An assembly as in claim 33 wherein said plurality of posts are integrally secured to respective ones of said arms and said two posts are substantially coplanar and said third post extending outwardly from the plane of said two posts.

35. An assembly as in claim 1 further comprising orientation means for maintaining a preferred orientation of an end portion of the vessel section engaged by said one clamp and including a base portion movably mounted adjacent one longitudinal side of at least one clamp and in communicating relation to an end portion of the vessel section engaged by said one clamp, said orientation means including a connecting means for attachment to the end portion of a vessel section protruding from said positioning means of said one clamp.

36. An assembly as in claim 35 wherein said base portion is movably connected to said securement means and selectively positionable relative thereto and between an operative position and an inoperative position relative to the vessel section engaged by said one clamp.

37. An assembly as in claim 35 wherein said orienting means comprises a plurality of posts secured to said base and including at least two of said posts disposed in spaced relation to one another on opposite sides of said positioning means and the end portion of the vessel section extending therefrom, said connecting means secured to said posts and positionable relative thereto into retaining engagement with the end portion of the vessel section.

38. An assembly as in claim 38 wherein said connecting means comprises a plurality of connectors at least equal in number to said posts and extending outwardly from respective ones of said posts into attachment with the end portion of the vessel section, said plurality of connectors engaging the end portions at a plurality of spaced locations about the end portions.

39. An assembly as in claim 38 wherein at least one of said connectors comprises an elongated, semi-rigid and flexible element movably mounted and selectively positionable into and out of an engaging position relative to the end portion of the vessel section.

40. An assembly as in claim 38 wherein at least one of said connectors comprise a thread of flexible material having one end secured to the end portions of the vessel and being secured to one of said posts a spaced distance from the end portion.

41. An assembly as in claim 37 wherein said plurality of posts comprises at least a third post secured to said base substantially between said two posts and including said connecting means connected thereto and extending outwardly therefrom into attachment with the end portion.

42. An assembly as in claim 37 wherein said connecting means comprises a plurality of connectors at least equal in number to said posts and extending outwardly from respective ones of said posts into attachment with the end portion of said vessel section, said plurality of connectors engaging the end portion at a plurality of spaced locations thereabout.

43. An assembly as in claim 42 wherein said plurality of posts are integrally secured to said base and said two posts are disposed in substantially coplanar relation to one another and said third post extends outwardly from the plane of the two posts in a substantially angular orientation.

44. An assembly as in claim 1 wherein at least one of said clamps comprises a second of said opposite ends of said two arms being free ends defining one end of said one clamp, said free ends spaced from one another at least partially by said fulcrum structure, each of said free ends disposed at a substantially common angular orientation relative to a remainder of respective ones of said arms.

45. An assembly as in claim 44 further comprising indentation means formed in an outer surface of each of said free ends for receipt of a pressure applying instrument thereto.

46. An assembly as in claim 1 wherein at least one of said clamps comprises a substantially linearly configured longitudinal side and an opposite longitudinal side being substantially convergent towards said first opposite ends of said arms from a point along the length of said clamp.

47. An assembly as in claim 46 wherein said convergently oriented side defines in part an inner side of said one clamp.

* * * * *